US00PP35647P2

(12) United States Plant Patent
Bean et al.

(10) Patent No.: US PP35,647 P2
(45) Date of Patent: Feb. 6, 2024

(54) ***PLECTRANTHUS* PLANT NAMED 'DE WET P'**

(50) Latin Name: *Plectranthus hybrid*
Varietal Denomination: De Wet P

(71) Applicant: De Wet Plant Breeders, Johannesburg (ZA)

(72) Inventors: Quinton Bean, Northriding (ZA); Charles Andrew De Wet, Sandton (ZA)

(73) Assignee: DE WET PLANT BREEDERS, Johannesburg (ZA)

( * ) Notice: Subject to any disclaimer, the term of this patent is extended or adjusted under 35 U.S.C. 154(b) by 0 days.

(21) Appl. No.: 18/208,230

(22) Filed: Jun. 9, 2023

(51) Int. Cl.
*A01H 5/02* (2018.01)
*A01H 6/50* (2018.01)

(52) U.S. Cl.
USPC ..... Plt./469

(58) Field of Classification Search
USPC ..... Plt./263.1, 469
See application file for complete search history.

*Primary Examiner* — Karen M Redden
(74) *Attorney, Agent, or Firm* — Penny J. Aguirre

(57) ABSTRACT

A new cultivar of *Plectranthus* plant named 'De Wet P' that is characterized by its 'De Wet P' exhibits large flowers that are deep pink in color. its floriferous blooming habit, its well-branched plant habit, and its vigorous growth habit.

2 Drawing Sheets

Botanical classification: *Plectranthus* hybrid.
Variety denomination: 'De Wet P'.

BACKGROUND OF THE INVENTION

The present invention relates to a new and distinct cultivar of *Plectranthus* of hybrid origin and will be referred to hereafter by its cultivar name, 'De Wet P'. 'De Wet P' is grown for use as a tender perennial landscape plant.

The new *Plectranthus* resulted from a breeding program conducted by the Inventors in Linbro Park, Johannesburg, South Africa. The goal of the breeding program was to develop new cultivars of *Plectranthus* with abundant, large flowers with good branching and strong and vigorous growth habits. The Inventors made crosses in April of 2018 between unnamed proprietary plants (not patented) of *Plectranthus* in the Inventors' breeding program as both the female parent and male parent. 'De Wet P' was selected as a single unique plant in October of 2020 from the resulting seedlings of the above cross.

Asexual propagation of the new cultivar was first accomplished by one of the Inventors by stem cuttings in October of 2020 in Linbro Park, Johannesburg, South Africa. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'De Wet P' as a unique cultivar of *Plectranthus*.

1. 'De Wet P' exhibits large flowers that are deep pink in color.
2. 'De Wet P' exhibits a floriferous blooming habit.
3. 'De Wet P' exhibits a well-branched plant habit.
4. 'De Wet P' exhibits a vigorous growth habit.

The male parent differs from 'De Wet P' in having flowers that are violet purple in color. The female parent differs from 'De Wet P' in having flowers that are paler pink in color. 'De Wet P' can be compared to the cultivars 'TNPLEVL' (U.S. Plant Patent Pending) and 'De Wet F' (U.S. Plant Pat. No. 31,501). 'TNPLEVL' differs from 'De Wet P' in having smaller flower that are paler pink in color with a white base and inflorescences that are less branched. 'De Wet F' is similar to 'De Wet P' in having large flowers and a dense and well-branched plant habit. 'De Wet F' differs from 'De Wet P' in having flowers that are purple in color and a shorter plant height.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the filing date. Disclosure includes but may not be limited to a website listing by Facebook, YouTube, The Gardener, Plants Management Australia, Four Seasons Nursery and Garden Center, and Greenleaf Nursery.

BRIEF DESCRIPTION OF THE DRAWINGS

The accompanying color photographs illustrate the overall appearance and distinct characteristics of a six-month-old plant of the new *Plectranthus* as grown in a conventional greenhouse in a 21-cm container in Linbro Park, Johannesburg, South Africa.

The photograph in FIG. 1 provides a side view of 'De Wet P' in bloom.

Figure 1:
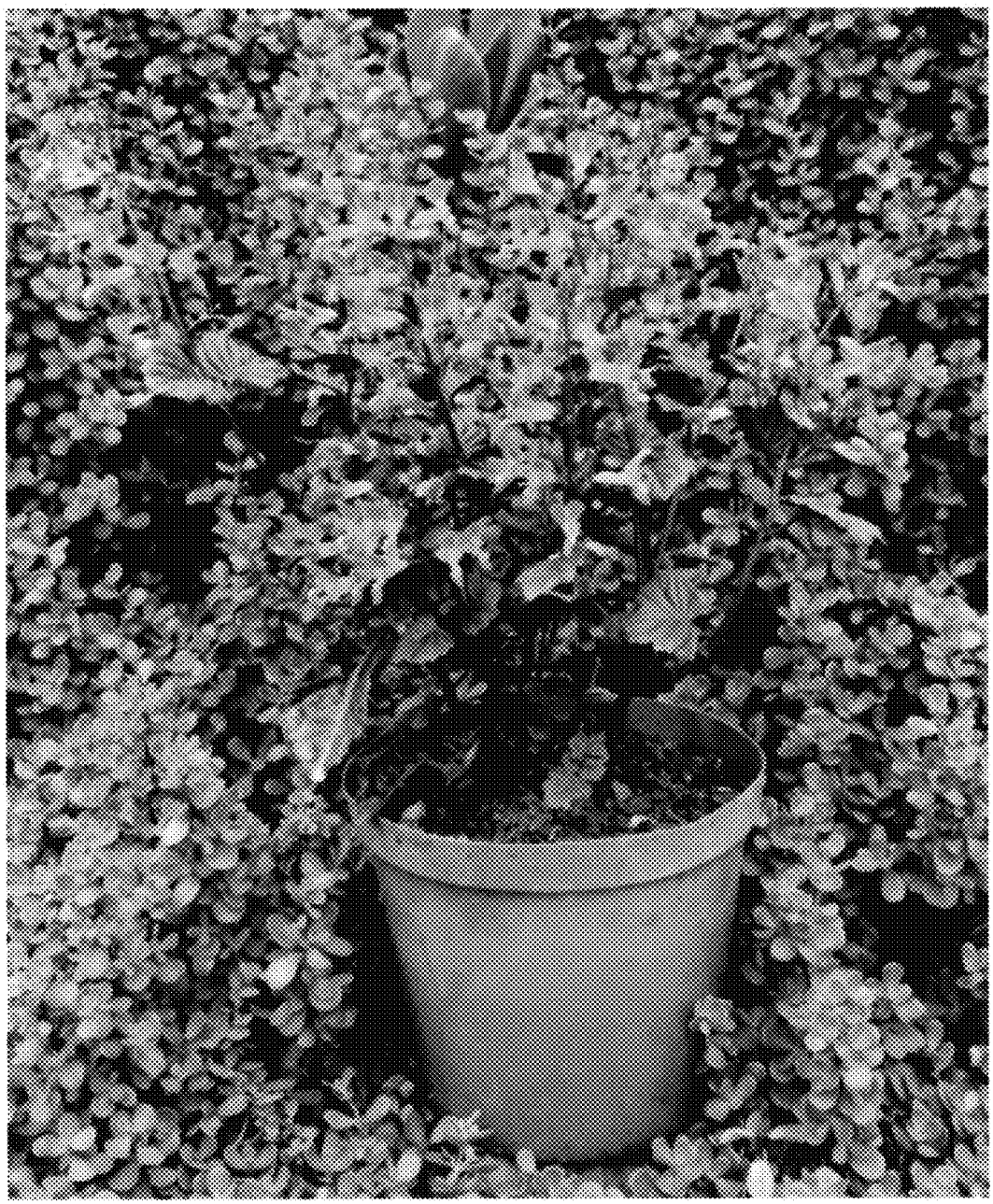
Figure 2:
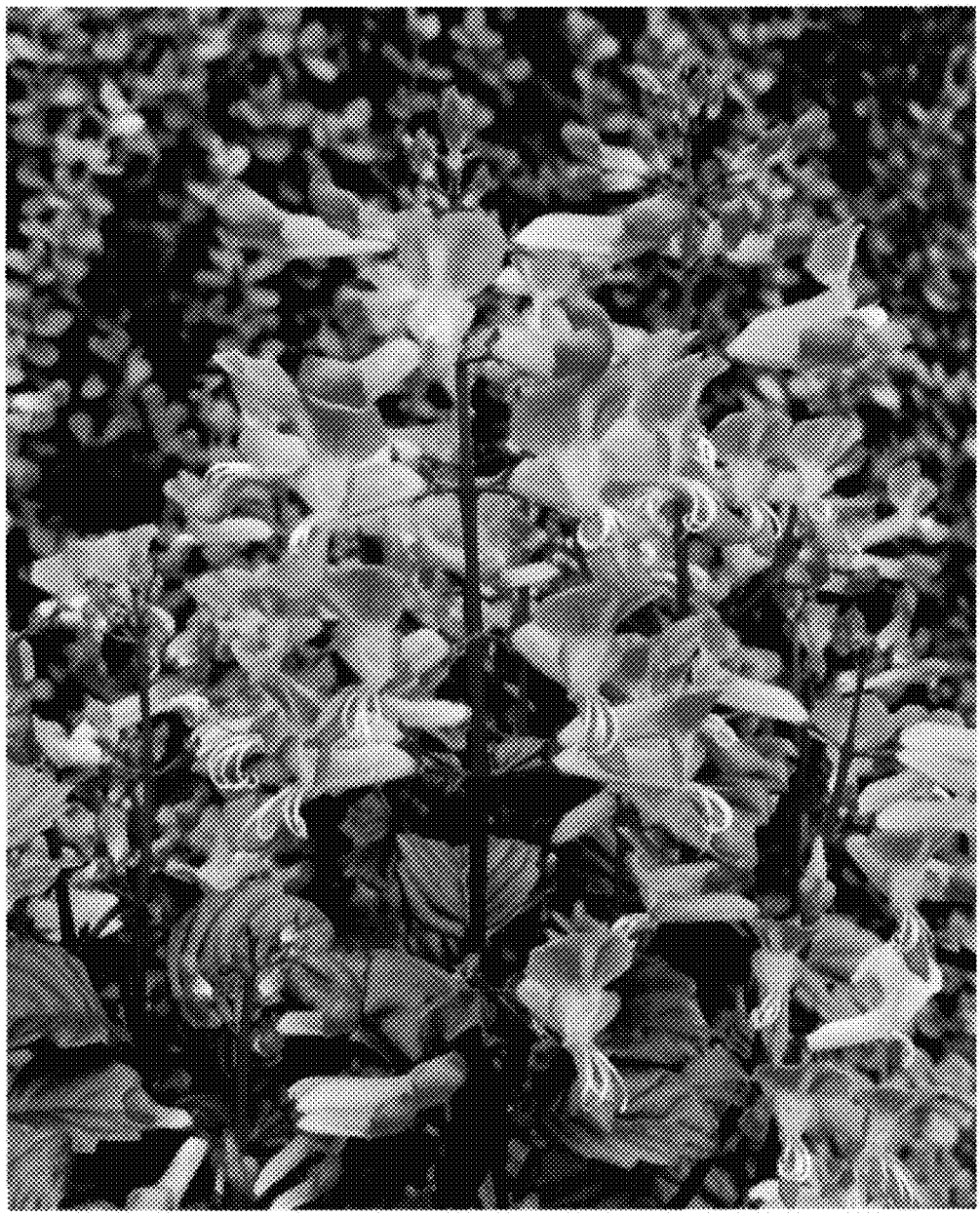

The photograph in FIG. 2 provides a close-up view of an inflorescences of 'De Wet P'.

The colors in the photographs are as close as possible with the digital photography techniques utilized and the color values cited in the detailed botanical description accurately describe the colors of the new *Plectranthus*.

DETAILED BOTANICAL DESCRIPTION

The following is a detailed description of seven-month-old plants of the new cultivar as grown in a conventional greenhouse in 3-qt containers in Loxly, Alabama. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—Blooms from mid-summer to mid-winter in South Africa, autumn in northern climates.

*Plant type.*—Perennial, evergreen subshrub.

*Plant habit.*—Upright and well branched.

*Height and spread.*—Average of 68 cm in height, 52 cm in width as grown in a one-gallon container, an average of 90 cm in height and 65 cm in width when grown in the landscape.

*Cold hardiness.*—At least in U.S.D.A. Zone 10.

*Diseases and pests.*—No susceptibility or resistance to pests or diseases has been observed.

*Root description.*—Densely fibrous, freely branched, 158C in color.

*Root development.*—5 to 6 weeks to initiate roots and an average of 5 weeks to produce a young plant from a rooted cutting.

*Propagation—Stem cuttings.*

*Growth rate.*—Vigorous.

Stem description:

*Stem shape.*—Quadrangular.

*Stem color.*—Young and mature stems a blend of 146A, 187A and N186A.

*Stem surface.*—Young and mature stems; glossy and densely pubescent covered with soft adpressed hairs; too small to measure size, matches stem surface.

*Stem size.*—Main branch; average of 30 cm in length, 8 mm in diameter, lateral branches; an average of 22 cm in length and 5 mm in diameter.

*Internode length.*—Ranging between 3 cm and 12 cm.

*Stem strength.*—Strong.

*Stem fragrance.*—When rubbed, moderately strong musty fragrance; typical for *Plectranthus*.

*Stem aspect.*—Upright, average angle of 35° from main branch.

*Branching.*—3 main stems and an average of 8 lateral branches per main stem.

Foliage description:

*Leaf shape.*—Ovate to broadly ovate.

*Leaf aspect.*—Slightly convex.

*Leaf division.*—Simple.

*Leaf base.*—Cuneate.

*Leaf apex.*—Acute.

*Leaf venation.*—Pinnate, color; upper surface matches leaf color, lower surface 187A.

*Leaf margins.*—Serrate.

*Leaf arrangement.*—Opposite.

*Leaf attachment.*—Petiolate.

*Leaf number.*—Average of 16 per lateral stem.

*Leaf surface.*—Upper and lower surface; glossy and moderately pubescent, covered with stiff, short hairs that are translucent, 0.4 mm in length, and match surface color.

*Leaf size.*—Up to 7 cm in length and 6 cm in width.

*Leaf color.*—Young upper surface; NN137A, mature upper surface; NN137A and 139A, young and mature lower surface; 194A, flushed with 187A.

*Leaf fragrance.*—Moderately strong musty fragrance, typical for *Plectranthus*.

*Petiole.*—An average of 2.5 cm in length and 1.5 mm in width, strong, color; a blend of N186C and NN137A, surface is glossy and densely covered with soft woolly translucent pubescence up to 1 mm in length and 187A n color.

Inflorescence description:

*Inflorescence type.*—Axillary and terminal racemes.

*Inflorescence number.*—1 per main stem and lateral stems.

*Lastingness of inflorescence.*—Flowers last an average of one week, self-cleaning.

*Inflorescence size.*—Up to 33 cm in height and 15 cm in width.

*Flower buds.*—Average of 4 mm in length and 2 mm in diameter, oblong in shape, glabrous and satiny surface, N75A in color.

*Flowers.*—Single, held outward to slightly upward, labiate in form, average of 3.5 cm in length, 2.5 cm in in diameter, tube; 2 cm in length, 6 mm in width, throat depth is shallow and 2 mm in length, average of 150 flowers per inflorescence.

*Flower fragrance.*—None.

*Petals.*—5; base fused into tube, 2 petals fused into one upper petal lobe, two lateral petal lobes and one lower petal lobe, upper petal lobe; rounded, obcordate in shape, base is fused into lateral petals and tube, held vertically, sides slightly cupped outward and rugose, 1.4 cm in length and 1.5 cm in width, margins are very slightly undulate, lateral petals; rounded, reniform in shape, 6 mm in length and 3 mm in width, margins are entire, held upright, base is fused into lateral petals and tube, lower petal; orbicular in shape, folded, 9 mm in length, 5 mm in width, margins undulate, base fused into tube, surfaces of all petal surfaces are glabrous, satiny and have a sheen and sparkling appearance, color: when opening and fully open upper and inner surface; N74C and N74A, tube when opening and fully open inner and outer surface; 69B.

*Calyx.*—5 mm in length and 3 mm in width, comprised of 5 sepals.

*Peduncles.*—Strong to moderately strong, average of 15 cm in length and 3 mm in diameter, terminal inflorescence held at an angle of 0° (vertical) and 45° for axillary inflorescences, a blend of 187B and N187A in color, surface is glossy and densely covered with stiff minute hairs that are translucent and shiny; minute in size, and either matching surface color or are NN155D in color.

*Pedicels.*—In pairs of 3, whorled down the peduncle, moderately strong, average of 6 mm in length and 1 mm in diameter, held at a 40° angle to horizontal to peduncle, a blend of 187B and N187A in color, surface is glossy and densely covered with stiff minute hairs that are translucent and shiny; minute in size, and either matching surface color or are NN155D in color.

Reproductive organs:

*Pistils.*—1, pistil; stigma; bifid, 0.5 mm in length and diameter, glabrous and matte surface, N78A in color, style; 2.5 cm in length, 0.75 mm in diameter, glabrous and shiny surface, color; top to mid-section 84C, mid-section to base NN155D, ovary; exterior, rounded, glabrous and glossy surface, 2 mm in diameter and length, 144A in color.

*Stamens.*—4, anthers; dorsifixed, oblong in shape, average of 1 mm in length and 0.5 mm in width, 203C in color, matte and glabrous surface, filament; 40% of lower section fused into flower tube, 60% free, aspect is straight to curled under, 2.7 cm in length, N155D in color, glabrous and shiny surface, slightly translucent, pollen; moderate in quantity, 155A in color.

*Fruit and seeds.*—No fruit or seed development has been observed.

It is claimed:

1. A new and distinct cultivar of *Plectranthus* plant named 'De Wet P' as herein illustrated and described.

* * * * *